United States Patent [19]

Hummel et al.

[11] Patent Number: 5,200,335
[45] Date of Patent: Apr. 6, 1993

[54] PHENYLETHANOL DEHYDROGENASE CAPABLE OF REDUCING ACETOPHENONE TO R(+)-PHENYLETHANOL

[75] Inventors: Werner Hummel, Titz; Maria-Regina Kula, Niederzier-Hambach, both of Fed. Rep. of Germany

[73] Assignee: Forschungszentrum Juelich GmbH, Juelich, Fed. Rep. of Germany

[21] Appl. No.: 694,988

[22] Filed: May 6, 1991

[30] Foreign Application Priority Data

May 7, 1990 [DE] Fed. Rep. of Germany ....... 4014573

[51] Int. Cl.$^5$ ........................ C12N 9/04; C12N 1/00
[52] U.S. Cl. .................................. 435/190; 435/853
[58] Field of Search ................................ 435/190, 853

[56] References Cited

PUBLICATIONS

Cripps et al., Eur. J. Biochem., vol. 86, No. 1, 1978, pp. 175–186, abstract.
Murakami Patent Abstracts of Japan, 11(150):C-422, 2597 (May 1987).
Aragozzini et al. "Stereoselective Reduction of Non–Cyclic Carbonyl Compounds by Some Eumycetes", Appl. Microbiol. Biotechnol., 24: 175–177 (1986).
Keinan et al. "Synthetic Applications of Alcohol–Dehydrogenase from Thermoanaerobium Brockii"; Ann. N.Y. Acad. Sci., 501: 130–149 (1987).

Primary Examiner—David M. Naff
Assistant Examiner—Mike Meller
Attorney, Agent, or Firm—Foley & Lardner

[57] ABSTRACT

A phenylethanol dehydrogenase capable of catalyzing the reduction of acetophenone to R(+)-phenylethanol in the presence of NADPH was isolated from Lactobacilli such as Lactobacillus kefir. The dehydrogenase is also capable of catalyzing the reduction of aromatic, alicyclic and aliphatic ketones selected from the group consisting of p-bromoacetophenone, methylcyclohexanone, acetone, methyl hexyl ketone, 4-phenyl-2-butanone, 1-phenyl-1,2-propanedione, ethyl pentyl ketone, pinacolone, propiophenone and p-chloroacetophenone. The dehydrogenase is rapidly inactivated by EDTA, but conventional inhibitors, chelators and SH-protecting reagents have only a slight effect on activity. The enzyme has a $K_M$ of $6 \times 10^{-4}$ M for acetophenone. The dehydrogenase is capable of catalyzing the enzymatic reduction of carbonyl compounds to form optically active hydroxy compounds in the presence of NADPH. In such reactions, NADPH can be simultaneously regenerated in the presence of glucose 6-P and glucose-6-P dehydrogenase or isopropanol.

4 Claims, 4 Drawing Sheets

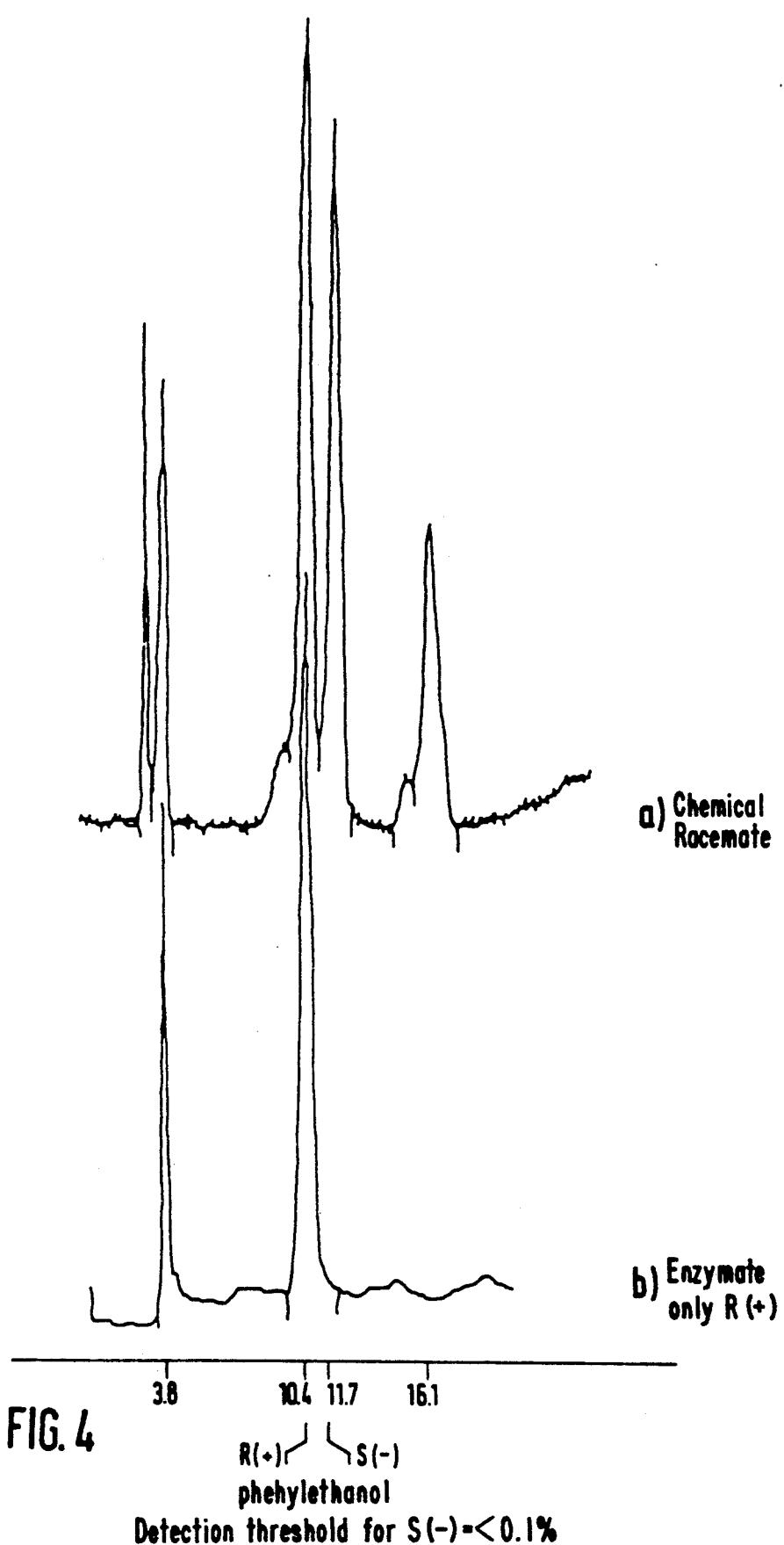

PHENYLETHANOL DEHYDROGENASE CAPABLE OF REDUCING ACETOPHENONE TO R(+)-PHENYLETHANOL

This invention relates to an enzyme that is capable of catalyzing the reduction of acetophenone to R(+)-phenylethanol and processes therefor.

BACKGROUND OF THE INVENTION

Optically active phenylethanol is a valuable chiral synthon which is difficult to obtain by conventional methods. A fermentation process for preparing S(−)-phenylethanol with dormant yeast cells was recently described by F. Aragozzini et al. (Appl. Microbiol. Biotechnol. (1986) 24, 175-177). Aragozzini reported the production of S(−)-phenylethanol from acetophenone (200 mg/l) after incubation for 48 hours (hr) with *Hansenula glucozyma* which yielded 52% (92% optically pure) and with *Torulopsis castellii* which yielded 20% (95% optically pure).

Although there are numerous descriptions in the literature of attempts to reduce acetophenone with commercially available alcohol dehydrogenases, from, for example, yeast, horse liver or *Thermoanaerobium brockii*, these enzymes can not convert acetophenone (see, for example, Keinan, E. et al. (1987) Ann. N.Y. Acad. Sci. 501, 130-149, Tab. 5). Enzyme-catalyzed processes for the synthesis of R(+)-phenylethanol have not been disclosed. Accordingly, the conversion of acetophenone to R(+)-phenylethanol by an enzyme-catalyzed process has been considered infeasible heretofore.

SUMMARY OF THE INVENTION

Accordingly, it is an object of the present invention to provide a phenylethanol dehydrogenase which is capable of reducing acetophenone to R(+)-phenylethanol.

Another object of the present invention is to provide a process for producing optically active hydroxy compounds by an enzymatic reduction of carbonyl compounds.

A further object of the present invention is to provide a means for the simultaneous regeneration of NADPH in a process for producing optically active hydroxy compounds by an enzymatic reduction of carbonyl compounds.

Another object of the present invention is to provide a process for producing and isolating a S(−)-alcohol from a racemic mixture of (R,S)-alcohol by an enzymatic oxidation of the racemic mixture.

A further object of the present invention is to provide a means for the regeneration of NADPH in a process for producing optically active hydroxy compounds by an enzymatic reduction of carbonyl compounds.

In accomplishing the foregoing objectives, there has been provided, in accordance with one aspect of the present invention, a phenylethanol dehydrogenase that catalyzes the reduction of acetophenone to R(+)-phenylethanol in the presence of NADPH and is isolated from Lactobacilli.

In accordance with still another aspect of the present invention, a dehydrogenase is provided that catalyzes the reduction of acetophenone to R(+)-phenylethanol in the presence of NADPH and is isolated from *Lactobacillus kefir*.

In accordance with another aspect of the present invention, a dehydrogenase is provided that catalyzes the reduction of acetophenone to R(+)-phenylethanol in the presence of NADPH and is isolated from *Lactobacillus kefir* strain DSM 20 587.

In accordance with yet another aspect of the present invention, there has been provided a phenylethanol dehydrogenase that catalyzes the reduction of acetophenone to R(+)-phenylethanol in the presence of NADPH, and (A) has an optimum pH of 7 for reduction of acetophenone and an optimum pH of 8 for oxidation of phenylethanol; (B) has an optimum temperature of 25°-30° C; (C) exhibits maximum enzyme activity for conversion of acetophenone at a concentration of 5.3 mM of the substrate; (D) has a $K_M$ value of $6 \times 10^{-4}$ mM for acetophenone; (E) exhibits maximum enzyme activity at a concentration of 190 μM NADPH; (F) is rapidly inactivated by EDTA but is only weakly inhibited by conventional inhibitors, chelators and SH-protecting reagents; (G) is capable of catalyzing the reduction of aromatic, alicyclic and aliphatic ketones selected from the group consisting of acetophenone, p-bromoacetophenone, methylcyclohexanone, acetone, methyl hexyl ketone, 4-phenyl-2-butanone, 1-phenyl-1,2-propanedione, ethyl pentyl ketone, pinacolone, propiophenone and p-chloroacetophenone.

In accordance with a further aspect of the present invention, a process has been provided for enzymatically reducing carbonyl compounds to form optically active hydroxy compounds, comprising reacting a carbonyl compound in the presence of NADPH with a dehydrogenase that catalyzes the reduction of acetophenone to R(+)-phenylethanol in the presence of NADPH and is isolated from Lactobacilli.

In accordance with another aspect of the present invention, a process has been provided for enzymatically reducing carbonyl compounds to form optically active hydroxy compounds, comprising the steps of reacting a carbonyl compound in the presence of NADPH with a dehydrogenase that catalyzes the reduction of acetophenone to R(+)-phenylethanol in the presence of NADPH and is isolated from Lactobacilli and which provides for the simultaneous regeneration of NADPH within the reaction mixture in the presence of glucose 6-P and glucose-6-P dehydrogenase.

In accordance with a further aspect of the present invention, a process has been provided for enzymatically reducing carbonyl compounds to form optically active hydroxy compounds by reacting a carbonyl compound in the presence of NADPH with a dehydrogenase that catalyzes the reduction of acetophenone to R(+)-phenylethanol in the presence of NADPH and is isolated from Lactobacilli and recovering the optically active hydroxy compounds from the reaction mixture.

In accordance with yet a further aspect of the present invention, a process has been provided for producing and separating S(−)-alcohol from a racemic mixture of (R,S)-alcohol comprising the steps of (A) reacting the racemic mixture with a dehydrogenase according to claim 1 in the presence of NADP+; and (B) separating R(+)-ketone as it is formed from unreacted S(−)-alcohol.

In accordance with another aspect of the present invention, a process for producing and separating S(−)-alcohol from a racemic mixture of (R,S)-alcohol comprising the steps of (A) reacting the racemic mixture with a dehydrogenase according to claim 1 in the presence of NADP+; and (B) separating R(+)-ketone as it is formed from unreacted S(−)-alcohol and wherein, NADP+ is regenerated by carrying out the reaction of said racemic mixture with said dehydrogenase in the presence of a ketone.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

In drawings which illustrate embodiments of the invention,

FIG. 4 shows the chiral separation of R(+)- and S(−)-phenylethanol of (a) a racemic mixture and (b) an enzymatic reaction product of acetophenone. The retention times of the reaction components are as follows:

Figure 1:
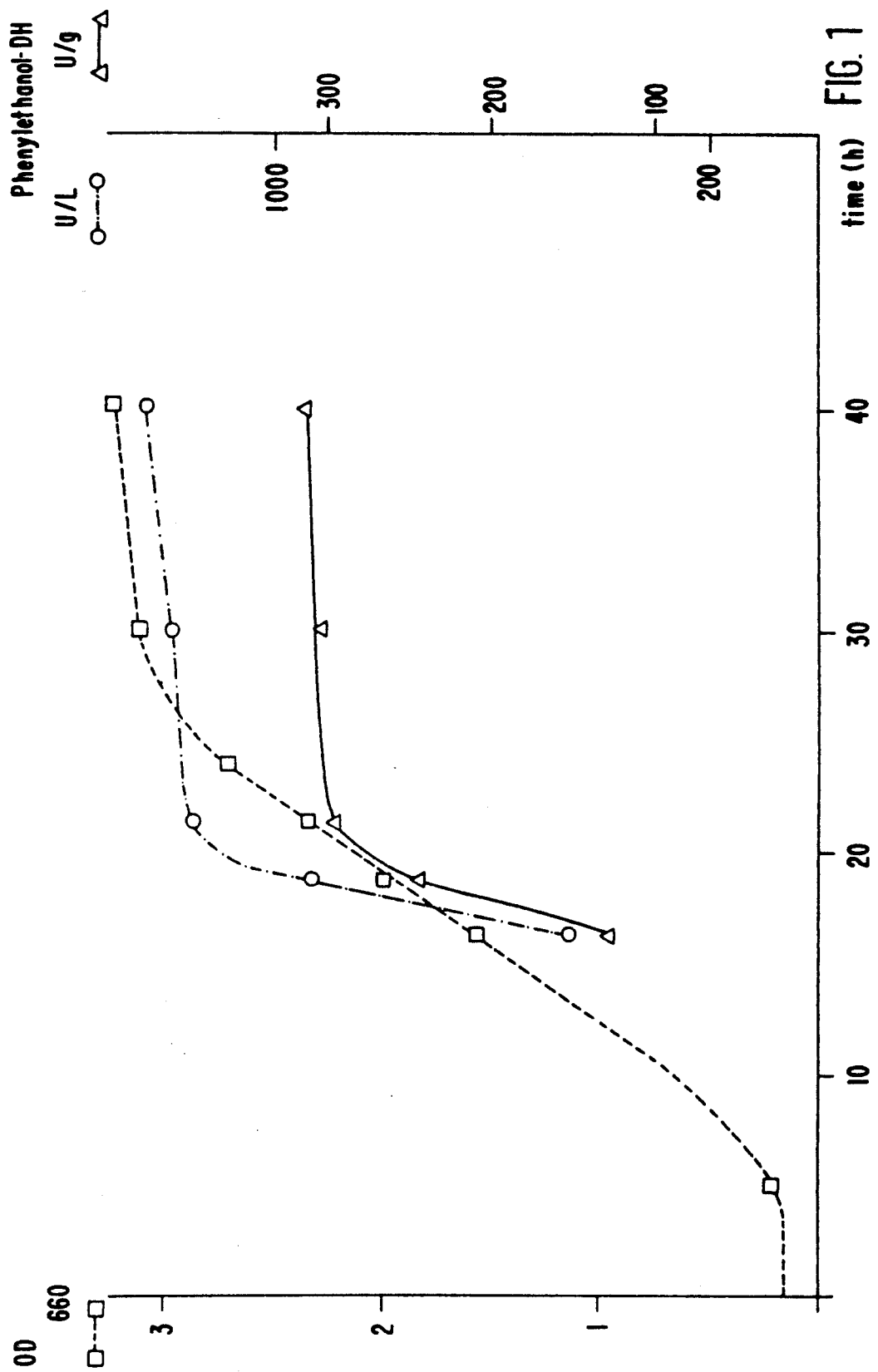
FIG. 1 shows the amount of phenylethanol dehydrogenase produced by the fermentation of *Lactobacillus kefir* as a function of time.

| |
|---|
| 3.8 min: derivatization reagent |
| 10.4 min: R(+)-phenylethanol |
| 11.7 min: S(−)-phenylethanol |
| 16.1 min: acetophenone). |

DETAILED DESCRIPTION OF THE PREFERRED EMBODIMENTS

It has been discovered that a phenylethanol dehydrogenase capable of producing R(+)-phenylethanol from keto compounds can be produced using microorganisms that synthesize the enzyme. Microorganisms possessing the ability to produce a phenylethanol dehydrogenase within the present invention include members of the genus Lactobacillus. A preferred species of this genus is *Lactobacillus kefir*. Exemplary of this preferred species is a strain of *Lactobacillus kefir*, designated DSM 20 587.

In order to isolate and purify a phenylethanol dehydrogenase within the present invention, a culture medium is inoculated with a species of Lactobacillus within the present invention. After incubating the culture, cells are harvested and then disintegrated.

In this description, a composition is said to "consist essentially of" a phenylethanol dehydrogenase according to the present invention when the salient enzymatic properties of that composition are determined by the presence of the phenylethanol dehydrogenase. Such a composition can be prepared by wet grinding with glass beads a suspension of cells harvested as described above. The resulting cell fragments are separated by conventional means from the enzyme containing liquid. Removal of cell fragments yields an enzymatically active liquid which consists essentially of the inventive enzyme and can be employed per se for purposes of the present invention. In other words, a phenylethanol dehydrogenase within the present invention is isolated when cell fragments are removed.

In a preferred embodiment, an enzyme within the present invention can be further purified by conventional means, such as ion exchange chromatography and gel filtration using $Mg^{++}$ ions. An inventive enzyme is thus provided in substantially pure form when the purification results in a significant increase in specific enzymatic activity, typically by at least an order of magnitude, relative to a crude preparation of disintegrated Lactobacillus cells (see Example 1).

Aromatic, alicyclic and aliphatic keto compounds are reduced to R(+)-phenylethanol by an enzyme according to the present invention. Exemplary of these compounds are p-bromoacetophenone, methylcyclohexanone, acetone, methyl-hexyl ketone, 4-phenyl-2-butanone, 1-phenyl-1,2-propanedione, ethyl- pentyl-ketone, pinacolone, propiophenone, and p-chloroacetophenone. In a preferred embodiment, acetophenone is reduced to R(+)-phenylethanol by an enzyme within the present invention. The product of the enzymatic reaction, R(+)-phenylethanol, can be further reacted as such without additional purification or, in a preferred embodiment, can be further purified by conventional means such as distillation or extraction methods.

A phenylethanol dehydrogenase particularly preferred for reducing acetophenone to R(+)-phenylethanol according to the present invention has the following characteristics:

an optimum pH of 7 for the reduction of acetophenone 7, and an optimum pH of 8 for the reverse reaction;

an optimum temperature of 25°–30° C;

maximum activity for the acetophenone conversion at 5.3 mM acetophenone, and a $K_M$ of $6 \times 10^{-4}$ M acetophenone;

maximum activity at 190 μM NADPH;

rapid inactivation by EDTA but conventional inhibitors, chelators and SH-protecting reagents have little effect on activity;

capable of reducing aromatic, alicyclic and aliphatic ketones, including, but not limited to acetophenone, p-bromoacetophenone, methylcyclohexanone, acetone, methyl hexyl ketone, 4-phenyl-2-butanone, 1-phenyl-1,2-propanedione, ethyl pentyl ketone, pinacolone, propiophenone and p-chloroacetophenone.

A phenylethanol dehydrogenase according to the present invention requires NADPH as coenzyme. Because the reaction equilibrium greatly favors the formation of the alcohol, the enzyme is particularly useful for synthesizing R(+)-phenylethanol or other secondary alcohols in a reaction in which the coenzyme is continuously regenerated. The following reaction is illustrative of this process:

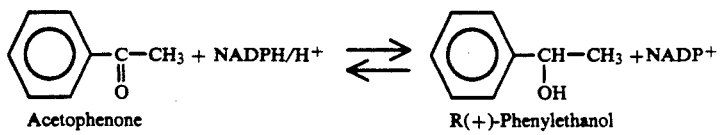

Acetophenone                  R(+)-Phenylethanol

The present invention also encompasses a process for the enzymatic reduction of carbonyl compounds with the resulting formation of optically active hydroxy compounds, wherein carbonyl compounds are reduced to phenylethanol in the presence of NADPH by an phenylethanol dehydrogenase according to the present invention. In a preferred embodiment, NADPH is simultaneously regenerated within the reaction mixture, in particular by means of glucose 6-P/glucose 6-P dehydrogenase.

The stereospecific enzymatic reaction can also be employed to obtain S(−)-alcohol by converting the R(+)alcohol from a racemic (R,S)-alcohol mixture in the presence of NADP. enzymatically by means of the phenylethanol dehydrogenase to a ketone, which can then easily be separated from the remaining S(−)-alcohol. In a preferred embodiment, NADP. is regenerate in an enzymatic reaction carried out utilizing an excess of a ketone which is both easy to separate and has a low $K_m$ value for the enzyme.

Without further elaboration, it is believed that one skilled in the art can, using the preceding description, utilize the present invention to its fullest extent. The following examples are, therefore, to be construed as merely illustrative, and not limitative of the remainder of the disclosure in any way whatsoever.

EXAMPLE 1

Production of Phenylethanol Dehydrogenase

A. Cultivation of *Lactobacillus kefir*

To obtain an enzyme according to the present invention, Lactobacillus kefir DSM 20 587 was cultured in the following medium (amount per liter):

| | |
|---|---|
| Glucose | 20 g |
| Yeast extract | 5 g |
| Universal peptone | 10 g |
| Meat extract | 5 g |
| Diammonium hydrogen citrate | 2 g |
| Sodium acetate | 5 g |
| Magnesium sulfate | 0.1 g |
| Manganese sulfate | 0.05 g |
| Dipotassium hydrogen phosphate | 2 g |
| Distilled H$_2$O | 1 L |

The pH of the solution was adjusted to 6.5, and the solution was then sterilized at 121° C. (2 bar) for 15 minutes. The microorganism was cultivated anaerobically, in an N$_2$ environment. On a 10 liter scale, the medium was inoculated with 300 ml of a 24 hour-old pre-culture of the microorganism after reaching a temperature of 30°. The change in enzyme activity with time was determined by removing aliquots of the culture at various times and measuring the activity of phenylethanol dehydrogenase after disruption of the cells. FIG. 1 shows the amount of phenylethanol dehydrogenase activity as a function of time. The enzyme activity level reached a maximum after a short period of time and persisted for a lengthy period.

On 70-liter scale, the microorganism was cultivated at room temperature for 75 hours, at a pH of 4.15 and an OD$_{660}$ of 4.12. After incubation, 320 grams of moist biomass were harvested by separation. The biomass can be stored at −20° C. without a detectable loss of activity over several months.

B. Phenylethanol dehydrogenase isolation (crude extract)

A phenylethanol dehydrogenase according to the present invention can be released from the cells by methods including, but not limited to ultrasound, high-pressure homogenization and wet grinding. In this case, the cells were disrupted by wet grinding with glass beads by suspending the biomass of bacteria (80 g) in 100 mM tris-HCl buffer (pH 9.0) with the addition of 0.1% 2-mercaptoethanol for a final concentration of moist biomass of 40% (final volume 200 ml). The cell constituents were released from the cooled suspension (4° C.) by mechanical disruption using a glass bead mill (DynoMill ®, supplied by Bachofen). Glass beads (0.5 mm) were introduced into the mill vessel, which had a capacity of 340 ml, to a volume of 290 ml (85% full). The disruption was carried out with the agitator shaft rotating at 2000 rpm. The cooling jacket and the agitator shaft bearings were cooled during disruption.

Eighty grams of the moist biomass yielded 138 ml of crude extract with an enzymatic activity of 35 U/ml and a protein content of 11 mg/ml. For purposes of this invention, 1 enzyme unit is the amount of enzyme which converts 1 μmol of substrate per minute. Based on the foregoing results, it is estimated approximately 27,000 units of phenylethanol dehydrogenase can be obtained from a 100-liter fermenter batch.

C. Purification of phenylethanol dehydrogenase

A phenylethanol dehydrogenase according to the present invention can be purified by ion exchange chromatography and gel filtration. The addition of Mg$^{2+}$ ions (i.e., chloride and sulfate salts) during the purification is required. An effective concentration is, for example, 0.1 mM MgCl$_2$. Without the addition of Mg$^{2+}$, the enzyme is completely inactivated during the purification and cannot be reactivated by subsequent addition.

(i) ION EXCHANGE CHROMATOGRAPHY: One milliliter of a crude extract prepared according to Example 1B was loaded onto a Mono-Q column (anion exchanger) (FPLC chromatography system, Pharmacia, Freiburg, FRG). The column was equilibrated with buffer A (0.05M potassium phosphate buffer, pH 7.0 containing 0.1 mM MgCl$_2$). After the column was thoroughly washed with buffer A, the phenylethanol dehydrogenase was eluted using a linear NaCl gradient (0–1M). The enzyme was eluted at about 0.35M NaCl. The results of this purification method are summarized in Table 1.

(ii) GEL FILTRATION: The fraction exhibiting the highest activity from the Mono-Q chromatography was further purified by chromatography on Superose 6 HR 10/30 (FPLC system, Pharmacia, Freiburg, FRG). Buffer A was used for equilibration and chromatography, and the chromatography was carried out at a flow rate of 0.5 ml/min. The results are summarized in Table 1.

TABLE 1

| Purification step | Enrichment of phenylethanol dehydrogenase | | | |
|---|---|---|---|---|
| | Total activ. U | Specif. activ. U/mg | Yield % | Concentration-fold |
| Crude extract | 16.9 | 1.4 | 100 | 1 |
| Mono-Q (anion ex.) | 14.5 | 28.3 | 86 | 20 |
| Superose (gel f.) | 12.8 | 99.1 | 76 | 70 |

EXAMPLE 2

Characterization of Phenylethanol Dehydrogenase

A. Effect of pH on phenylethanol dehydrogenase activity

Figure 2:
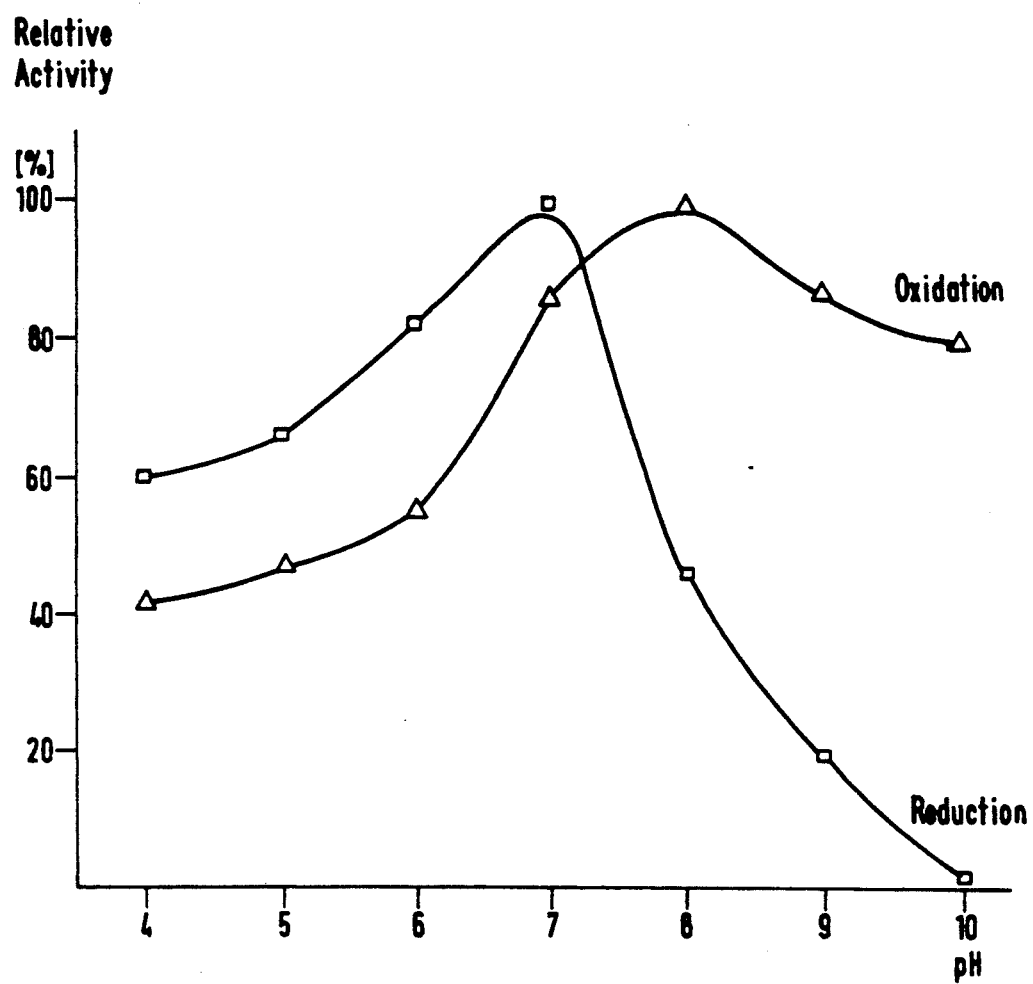
FIG. 2 depicts the effect of pH on the activity of phenylethanol dehydrogenase.

The effect of pH on phenyl dehydrogenase activity was determined by dissolving acetophenone (11 mM) in various 0.1M buffers, with pH values ranging from 4.0–10.0 (see FIG. 1). Twenty microliters of NADPH (8 mg/ml stock solution) and 10 µl of enzyme solution were added to 970 µl of each substrate solution and the activity was measured at 340 nm (30° C.). FIG. 2 shows the enzyme activity as a function of the pH. The optimum pH for the reduction of acetophenone was pH 7.0.

The optimum pH for the reverse reaction, the oxidation of phenylethanol, was measured in an analogous manner. (±)-Phenylethanol (22 mM) was dissolved in aliquots of a 0.1M buffer and the pH was adjusted to a range from 4.0 to 10.0. Twenty microliters of NADP. (165 mg/ml) and 10 µl of crude extract were added to each aliquot and the rate of NADPH formation was measured by photometry. FIG. 2 summarizes the results of these experiments. The optimum pH for oxidation of phenylethanol was 8.0.

B. Temperature optimum for the acetophenone reduction

The optimal assay temperature was determined by measuring the enzyme activity between 25 and 40° C. In each case, the assay mixture contained: (1) 970 µl acetophenone solution (5.5 mM in potassium phosphate buffer, pH 7.0 (final concentration equalled 5.3 mM); (2) 20 µl of NADPH (0.2 mM in the assay); and (3) 10 µl of the enzyme solution.

Table 2 summarizes the results of these experiments. The optimum temperature for the enzyme was 25°–30° C. Higher temperatures inactivated the enzyme.

TABLE 2

| Dependence of the enzyme activity on the assay temperature | |
|---|---|
| Temp. (°C.) | Enzyme activity (U/ml) |
| 25 | 21.0 |
| 30 | 19.5 |
| 35 | 9.5 |
| 40 | 0 |

C. Effect of various metal cations. inhibitors and SH-protecting reagents on enzyme activity Partially purified enzyme (after Mono-Q chromatography, concentrated 20-fold) was employed for the following tests.

(i) METAL CATIONS: The effect of $Mg^{2+}$, $Zr^{2+}$ and $Mn^{2+}$ ions was investigated using the assay mixture detailed below.

| | |
|---|---|
| 0.1M | potassium phosphate buffer, pH 7.0 |
| 5.5 mM | acetophenone |
| 0.2 mM | NADPH |
| 10 µl | of enzyme/ml (limiting concentration: 1 — 10 µg of protein/ml), $MgCl_2$, $ZnCl_2$ or $MnCl_2$ (final concentration of 1 mM) |

Enzyme activity was determined by measuring the change in NADPH concentration per minute as a function of the change in absorbance at 340 nm. Table 3 shows the stabilizing effect of cations, especially $Mg^{2+}$ ions.

(ii) INHIBITORS AND SH-PROTECTING REAGENTS: An assay mixture according to Example 2 C(i) without added metal cations but with addition of various inhibitors or SH-protecting reagents at a final concentration of 1 mM was used to determine the effect of certain enzyme inhibitors and SH-protecting reagents on enzyme activity. Due to its relative insolubility, p-hydroxymercurybenzoate was added at a final concentration of 0.1 mM. Phenylmethanesulfonyl fluoride was dissolved in acetonitrile to a final concentration of acetonitrile of mM. Acetonitrile alone had no effect on the enzyme activity in control tests.

The results are summarized in Table 3. While the enzyme was completely inhibited by the chelator EDTA, there was virtually no inhibition by chelators such as 1,10-phenanthroline and 2,2'-dipyridine. These results indicate that $Mg^{2+}$ ions are a necessary component of the enzyme. The relatively weak inhibition caused by inhibitors such as iodoacetamide, p-hydroxymercurybenzoate and N-ethylmaleimide suggests that the enzyme has no SH group in its active center. This hypothesis was confirmed by adding of SH-protecting reagents to no effect.

TABLE 3

| Effect of metal cations, inhibitors and SH-protecting reagents | |
|---|---|
| Addition | Activity remaining (%) |
| Metal cations: | |
| $MgCl_2$ | 132 |
| $ZnCl_2$ | 114 |
| $MnCl_2$ | 114 |
| Inhibitors and chelators: | |
| EDTA | 0 |
| 2,2'-Dipyridine | 106 |
| 1,10-Phenanthroline | 99 |
| Iodoacetamide | 90 |
| p-Hydroxymercurybenzoate | 92 |
| N-Ethylmaleimide | 81 |
| Phenylmethanesulfonyl fluoride (PMSF) | 94 |
| Triton X-100 | 94 |
| SH-Protecting reagents: | |
| Dithiothreitol | 95 |
| Glutathione | 99 |

D. Dependence of the reaction rate on the acetophenone concentration

To determine the optimal acetophenone concentration, enzyme activity was measured as a function of substrate concentration. The assay mixture employed is described below.

| | |
|---|---|
| 970 μl | acetophenone solution (in potassium phosphate buffer, pH 7.0) concentration varying between 50 and 7100 μM; |
| 20 μl | NADPH (8.0 mg/ml stock solution; concentration in the assay: 0.2 mM) |
| 10 μl | enzyme solution |

Activity was measured by photometry at 340 nm and 30° C. Values were corrected for substrate background reaction by measuring the absorbance of an aliquot of the assay mixture containing 970 μl of buffer in place of acetophenone solution. The maximum activity was reached at acetophenone concentrations of 5.3 mM (18.6 U/ml), and the $K_M$ of acetophenone was $6.0 \times 10^{-4}$ M. There was no excess substrate inhibition up to an acetophenone concentration of 10.6 mM.

E. Dependence of the reaction rate on the NADPH concentration

The reaction rate as a function of the NADPH concentration was measured. The following assay mixture was used:

| | |
|---|---|
| 970 μl | acetophenone solution (5.5 mM in potassium phosphate buffer, pH 7.0; final concentration in the assay: 5.3 mM) |
| 20 μl | NADPH (concentrations of 13 to 380 μM final concentration) |
| 10 μl | enzyme solution |

Enzyme activity was measured by photometry at 340 nm and 30° C. Maximum enzyme activity was measured at 190 μM NADPH (16.9 U/ml). The $K_M$ was $1.4 \times 10^{-4}$ M.

F. Phenylethanol dehydrogenase substrate spectrum

A series of aromatic and long-chain aliphatic ketones was tested in place of acetophenone as described in Example 2D to determine if they were suitable substrates for phenylethanol dehydrogenase-catalyzed reduction. The following assay mixture was employed:

| | |
|---|---|
| 970 μl | ketone solution (in potassium phosphate buffer, pH 7.0, at concentrations of 10 μM – 10 mM) |
| 20 μl | NADPH (8.0 mg/ml stock solution; final concentration of 0.2 mM) |
| 10 μl | enzyme solution (partially purified; 20-fold by Mono-Q chromatography) |

In a few instances, the concentration of the ketone was only 5 mM. The results are compiled in Table 4. The results show that the enzyme can catalyze the reduction of a large number of aromatic and aliphatic secondary ketones.

TABLE 4

| Substrate specificity of phenylethanol dehydrogenase | | |
|---|---|---|
| Substrates | $K_M$ (mM) | $V_{max}$ (%) |
| (A) NADPH-dependent reductions: | | |
| Aromatic compounds: | | |
| Acetophenone (methyl phenyl ketone) | 0.600 | 100 |
| Propiophenone (ethyl phenyl ketone) | 2.74 | 43 |
| 4-Phenyl-2-butanone | 9.40 | 90 |
| 4-Bromoacetophenone | 0.372 | 101 |
| 1-Phenyl-1,2-propanedione | n.d.* | 70 |
| Methyl 2-naphthyl ketone | n.d. | 11 |

TABLE 4-continued

| Substrate specificity of phenylethanol dehydrogenase | | |
|---|---|---|
| Substrates | $K_M$ (mM) | $V_{max}$ (%) |
| Benzaldehyde | n.d. | 10 |
| 4-Chloroacetophenone | 0.390 | 93 |
| Cyclic and acyclic aliphatic comp.: | | |
| (±)-Methylcyclohexanone | 70.0 | 109 |
| Pinacolone (tert-butyl methyl ketone) | 3.38 | 53 |
| Methyl hexyl ketone | 0.251 | 91 |
| Ethyl pentyl ketone | 0.681 | 66 |
| Mesityl oxide (4-methyl-3-pentene-2-one) | n.d. | 12 |
| Acetone | 37.9 | 96 |
| NADPH | 0.14 | 100 |
| (B) NADP+-dependent oxidations: | | |
| R(+)-Phenylethanol | 3.5 | 11 |
| (±)-Phenylethanol | 4.3 | 17 |
| Isopropanol | 0.117 | 18 |
| NADP+ | 0.19 | 17 |

*not determined

EXAMPLE 3

Enzyme-catalyzed batch preparation of (±)-phenylethanol

A 10 mM solution of acetophenone was reacted with 0.5 U/ml of the phenylethanol dehydrogenase and 0.05 mM of coenzyme with a final volume of 5 ml. The NADPH coenzyme was regenerated by coupling it with glucose 6-phosphate (15 mM) and glucose-6-phosphate dehydrogenase (0.5 U/ml). Fifty microliter aliquots taken at intervals of 10 min were analyzed by HPLC to determine the relative amounts of phenylethanol and acetophenone present in the reaction mixture.

Fifty microliters of acetone was added to each of the aliquots and the precipitated protein was removed by centrifugation. Fifty microliters of the supernatant was mixed with 450 μl of the HPLC eluent.

| HPLC conditions: | |
|---|---|
| Column: | ODS-Hypersil 5μ (250 × 4.6 mm) |
| eluent: | tris-HCl pH 8.4 containing 35% acetonitrile (filtered and gassed with helium) |
| flow rate: | 1 ml/min |
| temperature: | 25° C. (cooling cabinet) |
| detection: | photometry at 226 nm |
| sample quantity: | 40 μl |
| elution times: | acetophenone = 12.6 min, phenylethanol = 7.8 min |

Figure 3:
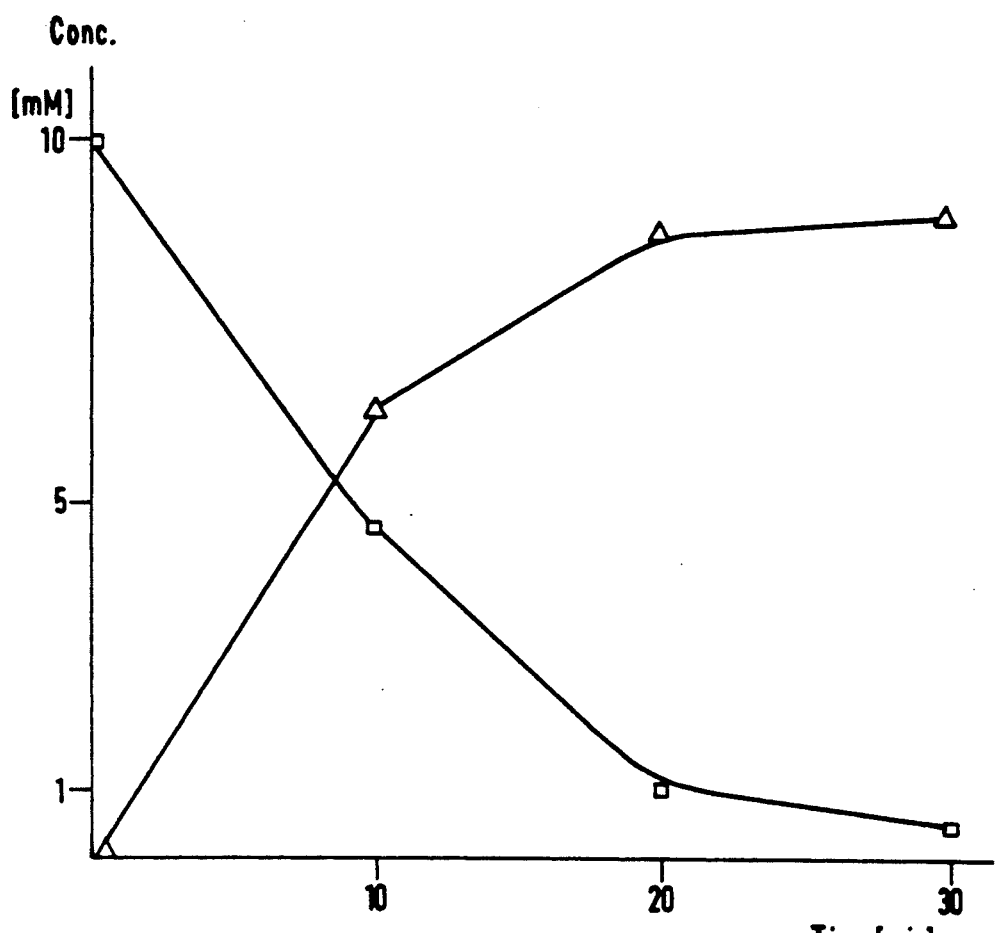
FIG. 3 shows the relationship of the amount of acetophenone versus phenylethanol present over time in a batch fermentation reaction.

FIG. 3 shows that, during the reaction, there was a continuous decrease in the concentration of acetophenone from an initial concentration of 10 mM to an ending concentration of approximately 0.5 mM. The decrease in the concentration of acetophenone was proportional to the increase in concentration of phenylethanol.

Alternative methods for regenerating the coenzyme NADPH were tested in two other experiments. In the first alternative method, a 20 mM solution of acetophenone was reacted with 0.5 U/ml of phenylethanol dehydrogenase and 0.05 mM of coenzyme in a total volume of 5 ml. The coenzyme NADPH was regenerated by coupling it with glucose (15 mM) and glucose dehydrogenase (0.5 U/ml).

In the second alternative method, a 20 mM solution of acetophenone was reacted with 0.5 U/ml of phenylethanol dehydrogenase and 0.05 mM of coenzyme in a total volume of 5 ml. The coenzyme NADPH was regenerated by coupling it with isopropanol (20 mM). Isopropanol is another substrate of a phenylethanol dehydrogenase according to the present invention, due to the stoichiometric formation of acetone and the reduction of $NADP^+$.

In both alternative methods, aliquots were analyzed every 10 minutes to determine the concentration of phenylethanol by HPLC as described above. Representative results of these methods of regenerating the coenzyme are compiled in Table 5.

TABLE 5

Reaction of 10 mM acetophenone in the presence of various means for regenerating NADPH (DH = dehydrogenase)

| NADPH regeneration by | Phenylethanol (mM) after | | |
|---|---|---|---|
| | 10 min | 30 min | 60 min |
| Glucose/Glucose-DH | 1.8 | 3.8 | 7.9 |
| Glucose 6-P/Glucose-6-P DH | 6.2 | 8.8 | 8.6 |
| Isopropanol | 1.6 | 4.6 | 8.0 |

EXAMPLE 4

Enzyme-catalyzed preparation of (±)-phenyl-ethanol in an enzyme membrane reactor It was determined that the continuous synthesis of phenylethanol was possible using an enzyme membrane reactor. In an enzyme membrane reactor, the enzymes were retained by an ultrafiltration membrane (YM 5 from Amicon, Witten, FRG) in the reactor (CEC 1 from Amicon), while the low molecular weight constituents in the reaction solution such as the unreacted substrate, product and buffer, were continuously removed from the solution. The residence time was 2 hours. The reaction volume was kept constant by replenishing the solution of 10 mM acetophenone in buffer (0.1M potassium phosphate, pH 7.0) at the same rate the ultrafiltrate was removed from the reactor. The reactor volume of 10 ml was comprised of the following constituents:

| 0.5 U/ml | phenylethanol dehydrogenase |
| 0.5 U/ml | glucose-6-phosphate dehydrogenase |
| 5 mM | glucose 6-phosphate |
| 10 mM | acetophenone |
| 0.4 mM | $NADP^+$ in 0.1M potassium phosphate buffer (pH 7.0) |

$NADP^+$ and glucose 6-phosphate were replenished in the reaction vessel every 4 hours to maintain the concentrations listed above.

The reaction was monitored by measuring the concentration of acetophenone and phenylethanol in aliquots approximately every 3 hours by HPLC according to the method described in Example 3. The results are summarized in Table 6.

TABLE 6

Continuous conversion of acetophenone into phenylethanol in an enzyme membrane reactor

| Time (h) | Acetophenone (mM) | Phenylethanol (mM) |
|---|---|---|
| 0 | 10 | 0 |
| 1 | 3.8 | 5.2 |
| 4 | 2 | 6.9 |
| 8 | 0.8 | 7.8 |
| 26 | 0.6 | 7.7 |
| 32 | 0.2 | 8.7 |

TABLE 6-continued

Continuous conversion of acetophenone into phenylethanol in an enzyme membrane reactor

| Time (h) | Acetophenone (mM) | Phenylethanol (mM) |
|---|---|---|
| 46 | 0.2 | 8.6 |
| 52 | 0.2 | 8.4 |

EXAMPLE 5

Demonstration of the stereospecificity of the enzyme

Two methods were used to demonstrate the stereospecificity of the enzyme and the enantiomeric purity of the product. In one method, an enzymatically prepared product was analyzed using a chiral HPLC to separate R(+)- and S(−)-phenylethanol. In a second method, oxidation of commercially available pure isomers of R(+)- and S(−)-phenylethanol by a phenylethanol dehydrogenase according to the present invention was measured by photometry.

A. Chiral HPLC

In order to obtain relatively large amounts of enzymatically prepared product for this analysis, the product was prepared by the continuous reaction of acetophenone with regeneration of the coenzyme NADPH according to the method described in Example 4. Separation of the two enantiomers under the experimental conditions was possible only after derivatization of phenylethanol to the benzoyl derivative. To produce the benzoyl derivative, 1 ml of the product solution was extracted by shaking with 1 ml of dichloromethane. After the aqueous phase had been separated off, dichloromethane was removed and 1 ml of pyridine was added. For the derivatization, 5 µl of benzoyl chloride was added, and the mixture was allowed to stand at room temperature for 30 minutes. To this reaction mixture, 0.5 ml of $H_2O$ was added and then the product was extracted with 2 ml of hexane and analyzed by HPLC.

HPLC Conditions:

| Column: | Nucleosil Chiral 2 (250 × 4 mm) from Macherey and Nagel (Düren, FRG) |
| eluent: | n-heptane containing 0.05% 1-propanol and 0.05% trifluoroacetic acid (residual water was removed with 4 Å molecular sieves) |
| temperature: | 25° C. (cooling cabinet) |
| flow rate: | 1 ml/min; detection by spectrophotometry at 250 nm |
| sample loop: | 40 µl |

The product peak at 10.4 minute was determined by carrying out the derivatization with commercially available pure compounds of R(+)- and S(−)-phenylethanol (Fluka).

The results are presented in FIG. 4 which shows that pure R(+)-phenylethanol was obtained by enzymatic reduction while S(−)-phenylethanol was undetected.

B. Reverse reaction with R(+)- or S(−)-phenylethanol

The following assay mixtures were employed to demonstrate stereospecificity by photometry:

| (I) | 970 | µl of R(+)-phenylethanol (11 mM; in potassium phosphate buffer |

| | | -continued |
|---|---|---|
| | | 0.1M, pH 8.0) |
| | 20 | μl of NADP+ (165 mg/ml) |
| | 10 | μl of enzyme solution |
| (II) | 970 | μl of S(−)-phenylethanol |
| | | (11 mM; in potassium phosphate buffer 0.1M, pH 8.0) |
| | 20 | μl of NADP+ (165 mg/ml) |
| | 10 | μl of enzyme solution |

A third mixture containing 22 mM (±)-phenylethanol was employed for comparison. Enzyme activity was measured by photometry at 340 nm at 30° C. The results are shown below:

| Mixture I: | 3.5 U/ml |
|---|---|
| Mixture II: | 0 |
| Mixture III: | 2.3 U/ml |

The results clearly show that a phenylethanol dehydrogenase according to the present invention is highly specific for R(+)-phenylethanol. Comparing the results obtained with mixture I to those of mixture III shows that the simultaneous presence of S(−)-phenylethanol inhibits the enzyme.

EXAMPLE 6

Preparation of S(−)-alcohols

A phenylethanol dehydrogenase according to the present invention which was obtained from *Lactobacillus kefir* was used to prepare S(−)-alcohols using a racemic mixture of the alcohol, [(R,S)-phenylethanol] as the substrate. The R group was enzymatically oxidized to the corresponding ketone. In this process, it was advantageous if the ketone, such as acetone, was also a substrate of the enzyme, so that the NADPH which was formed could be oxidized, which provided for an increase in the rate of the reaction. Only small amounts of the coenzyme were required. Results of experiments to produce S-phenylethanol are summarized in equations (1)–(3).

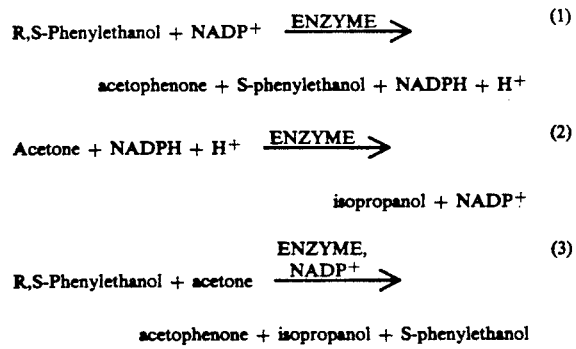

The components listed in Table 6 were employed in the preparation of S(−)-phenylethanol.

TABLE 6

Conditions for the enzymatic preparation of S-phenylethanol for R,S-phenylethanol

| Component | Reaction A | Reaction B |
|---|---|---|
| | (Final concentration) | |
| R,S-Phenylethanol | 5 mM | 5 mM |
| Potassium phosphate buffer (0.4M; pH 7.0) | 875 μl | 875 μl |
| MgCl₂ × 6 H₂O | 0.1 mM | 0.1 mM |
| NADP+ | 1 mM | 1 mM |
| Phenylethanol dehydrogenase (28 U/mg) | 0.6 U | 0.6 U |
| Acetone | — | 10 mM |

The reaction mixture was incubated at 30° C., and aliquots were measured according to the HPLC described in Example 3 at 0, 10 and 30 minutes to determine the concentration of phenylethanol and acetophenone. The results are presented in Table 7.

TABLE 7

Enzymatic reaction of R,S-phenylethanol (5 mM)

| Mixture | Reaction time (min) | Acetophenone (mM) | Phenylethanol (mM) |
|---|---|---|---|
| A | 0 | 0 | 5 |
| A | 10 | 0.21 | 4.79 |
| A | 30 | 0.38 | 4.62 |
| B | 0 | 0 | 0 |
| B | 10 | 0.50 | 4.50 |
| B | 30 | 0.88 | 4.12 |

What is claimed is:

1. An isolated phenylethanol dehydrogenase that selectively catalyzes the reduction of acetophenone in solution to essentially pure R(+)-phenylethanol in the presence of NADPH, and wherein said dehydrogenase, in substantially pure form,
   (A) has an optimum pH of 7 for reduction of acetophenone and an optimum Ph of 8 for oxidation of phenylethanol;
   (B) has an optimum temperature of 25°–30° C.;
   (C) has a $K_M$ value of $6 \times 10^{-4}$ M for acetophenone;
   (D) has a $K_M$ value of $1.4 \times 10^{-4}$ M for NADPH; and
   (E) is rapidly inactivated by EDTA but is only weakly inhibited by inhibitors and chelators selected from the group consisting of 2,2'-dipyridine, 1,10-phenanthroline, iodoacetamide, p-hydroxymercurybenzoate, N-ethylmaleimide, phenylmethanesulfonyl fluoride and Triton X-100 and SH-protecting reagents selected from the group consisting of dithiothreitol and glutathione.

2. The dehydrogenase of claim 1, wherein said dehydrogenase is isolated from *Lactobacillus kefir*.

3. The dehydrogenase of claim 1, wherein said dehydrogenase is isolated from *Lactobacillus kefir* strain DSM 20 587.

4. The dehydrogenase of claim 1, wherein said dehydrogenase is capable of catalyzing the reduction of aromatic, alicyclic and aliphatic ketones selected from the group consisting of acetophenone, p-bromoacetophenone, methylcyclohexanone, acetone, methyl hexyl ketone, 4-phenyl-2-butanone, 1-phenyl-1,2-propanedione, ethyl pentyl ketone, pinacolone, propiophenone and p-chloroacetophenone.

* * * * *